(12) United States Patent
Saito et al.

(10) Patent No.: US 8,173,711 B2
(45) Date of Patent: May 8, 2012

(54) AGENT FOR RELIEF OR PREVENTION OF XEROSTOMIA

(75) Inventors: Ichiro Saito, Tokyo (JP); Kenji Fujii, Kobe (JP); Kazuya Hamada, Kobe (JP)

(73) Assignees: Kaneka Corporation, Osaka (JP); Ichiro Saito, Tokyo (JP)

( * ) Notice: Subject to any disclaimer, the term of this patent is extended or adjusted under 35 U.S.C. 154(b) by 439 days.

(21) Appl. No.: 12/524,931

(22) PCT Filed: Jan. 31, 2008

(86) PCT No.: PCT/JP2008/051550
§ 371 (c)(1),
(2), (4) Date: Sep. 28, 2009

(87) PCT Pub. No.: WO2008/093793
PCT Pub. Date: Aug. 7, 2008

(65) Prior Publication Data
US 2010/0028318 A1    Feb. 4, 2010

(30) Foreign Application Priority Data
Jan. 31, 2007    (JP) ................................ 2007-022153

(51) Int. Cl.
*A61K 31/045*    (2006.01)
(52) U.S. Cl. ....................................... 514/728
(58) Field of Classification Search .................. 514/728
See application file for complete search history.

(56) References Cited

U.S. PATENT DOCUMENTS

| 2002/0054857 A1 | 5/2002 | Shuch et al. |
| 2007/0196349 A1 | 8/2007 | Kitamura et al. |

FOREIGN PATENT DOCUMENTS

| EP | 1 281 398 | 2/2003 |
| EP | 1 790 238 | 5/2007 |
| JP | 7-330584 | 12/1995 |
| JP | 7-330593 | 12/1995 |
| JP | 10-287560 | 10/1998 |
| JP | 2004-532831 | 10/2004 |
| JP | 2006-70016 | 3/2006 |
| WO | 02/076433 | 10/2002 |

OTHER PUBLICATIONS

Examiner Timur Albayrak, Supplementary European Search Report issued by the European Patent Office in European Application No. 08710660.5 and mailed Mar. 23, 2010—5 pages.

English translation of International Preliminary Report on Patentability issued in International Application No. PCT/JP2008/051550 and mailed Aug. 4, 2009—6 pages.

Porter, et al., "An update of the etiology and management of xerostomia", Oral Surg Oral Med Oral Pathol Oral Radiol Endod, vol. 97, No. 1, Jan. 2004, pp. 28-46.

Von Bütizingslöwen, et al., "Salivary dysfunction associated with systemic diseases: systematic review and clinical management recommendations", Oral Surg Oral Med Oral Pathol Oral Radiol Endod, vol. 103, No. 3, Suppl. 1, Mar. 2007, pp. S57.el-15.

*Primary Examiner* — Raymond Henley, III
(74) *Attorney, Agent, or Firm* — Hamre, Schumann, Mueller & Larson, P.C.

(57) ABSTRACT

The present invention has its object to provide a safer and highly effective composition capable of relieving or preventing xerostomia. The present invention relates to an agent for relieving or preventing xerostomia comprising an oxidized coenzyme Q and/or a reduced coenzyme Q as active ingredients, a composition containing the agent for relieving or preventing xerostomia in a form of a food product, a health food, a dietary supplement, a supplement, an oral health care product, a medicament, a quasi drug, a pet food, a feed or the like, and a method for treating xerostomia and a method for reducing risks of xerostomia comprising administering the composition.

4 Claims, No Drawings

AGENT FOR RELIEF OR PREVENTION OF XEROSTOMIA

TECHNICAL FIELD

The present invention relates to an agent for relieving or preventing xerostomia (dry mouth). More specifically, the present invention provides an agent for relieving or preventing xerostomia (dry mouth), which contains a coenzyme Q as an active ingredient, and is suitable for relieving or preventing various xerostomia-associated symptoms caused by decreased salivary secretion due to various causes.

BACKGROUND ART

A condition generally called Xerostomia or dry mouth is characterized by diminished or deficient salivary secretion induced by various causes, and commonly occurs. Since so many factors are involved in salivary secretion, it is remarkably difficult to find out causes of xerostomia. Examples of known causes of this condition include various diseases causing organic change of salivary glands; pathological changes of salivary glands caused by systemic diseases; damaged salivary glands owing to radiotherapy; HIV infection (AIDS); secretory hypofunction owing to aging; and effects of administration of various drugs. In addition, this condition is known to be brought on by mental fatigue or stress under complicated environment in social life.

Symptoms of xerostomia are usual, especially among elderly people. Approximately 16% of males and 25% of females in a group of elderly people aged 70 or older have symptoms of xerostomia. This may be because of regressive change of salivary glands owing to aging, and decreased salivary secretion associated with this change. Effects of various drugs are also pointed out as causes of xerostomia. Examples of drugs that may cause xerostomia include: diuretics such as trichloromethiazide and furosemide, hypotensors such as reserpine and clonidine hydrochloride, anticholinergic agents such as atropine sulfate, and antihistamines such as chlorophenylamine maleate. Other examples thereof include various expectorant/cough suppressants, anti-Parkinson drugs, psychotropic drugs, antidepressants, tranquilizers and muscle relaxants. Radiotherapy has become increasingly important for treating malignant tumors in oral surgery and otolaryngology fields, and almost inevitably causes severe damage to salivary glands by radioactive rays owing to the irradiation area. This damage often results in especially severe xerostomia. The number of patients suffering from xerostomia is expected to increase with widespread use of the radiotherapy.

Patients with xerostomia have a dry feeling in the mouth, and also may experience symptoms such as a burning feeling in the mouth, oral pain, glossodynia, dysgeusia, atrophy of lingual-papillae, oral mucosal inflammation, mouth sores, ulcers, cracked tongues, cracked mouth corner, other difficulties in mastication, swallowing, phonation and speech, interrupted sleep and eating disorder. Some patients have to take nourishment into their bodies by way of tube feeding or intravenous drip. Xerostomia causes dental disorders including oral mucous membrane ulcers, dental caries and periodontosis, oral infections and respiratory tract infections at an increased frequency, and also causes bad breath. There is a strong demand for appropriate solutions to these problems.

As a product for relieving xerostomia, artificial saliva, gargles, moisturizing mouthwashes containing hyaluronic acid and chondroitin sulfate, and the like are currently used, and can only temporarily hydrate the mouth. Salivary secretion accelerators (e.g. cevimeline hydrochloride) or various Kampo medicines also have been used for the purpose of relieving xerostomia. However, the use thereof causes unfavorable side effects in some cases, and does not deliver sufficient effects for relieving or preventing xerostomia.

Coenzyme Q is known to be subcategorized into coenzyme $Q_1$ to coenzyme $Q_{13}$ according to the repetitive structure of the side chain. Coenzyme $Q_{10}$ is the predominantly occurring form of coenzyme Q in many mammals, and therefore coenzyme $Q_{10}$ occurs in humans. Coenzyme Q is topically present in mitochondria, lysosomes, Golgi bodies, microsomes, peroxisomes, cell membranes or the like, and it is essential for maintaining functions in living bodies because coenzyme Q is known to be involved in activation of ATP production as a component of the electron transfer system in mitochondria, and antioxidant action and stabilization of membranes in vivo. Coenzyme Q is known to transfer electrons by repeating oxidation and reduction in the electron transfer system.

It is known that coenzyme Q can be in an oxidized form and a reduced form. The oxidized coenzyme is named "ubiquinone", and the reduced coenzyme is named "ubiquinol". Coenzyme Q in vivo is mostly in the reduced form since coenzyme Q in the oxidized form is absorbed in the body to be intracellularly converted into the reduced form by a reductase. Reduced coenzyme Q provides antioxidant action when reacting with active oxygen in the body. Namely, reduced coenzyme Q exhibits antioxidant activity. Reduced coenzyme Q is regarded as a main active ingredient in vivo based on the above-mentioned facts that coenzyme Q is mostly in the reduced form in vivo and only the reduced coenzyme Q exhibits antioxidant activity.

Reduced coenzyme Q is, however, easily oxidized in air and thereby converted into oxidized coenzyme Q. Therefore, the stability of reduced coenzyme Q in air is problematic. For this reason, only oxidized coenzyme Q has been industrially utilized owing to its favorable stability in air. Based on this background, the term "coenzyme Q" in previous documents generally indicates oxidized coenzyme Q, unless otherwise specified. The reduced coenzyme is described as "ubiquinol" or "reduced coenzyme Q" instead of being simply described as "coenzyme Q".

Oxidized coenzyme Q has been conventionally used as an adjuvant for congestive heart failure. In recent years, oxidized coenzyme Q is widely used in health foods all over the world. Oxidized coenzyme Q has been widely studied on its physiological activities and is known to have various physiological activities such as anti-diabetes, anti-fatigue and anti-arteriosclerosis activities (See Patent Documents 1 to 3). There have been very few reports on side effects of this compound. A safety test in animals in which this compound was administered to rats for 52 consecutive weeks at a high dose of 1.2 g/kg/day resulted in no evidence of toxicity, and thereby proved high safety of this compound (See Non-Patent Document 1).

Oxidized coenzyme Q was reported to exhibit effects to improve conditions of Parkinson's disease model mice, one of typical neurodegenerative diseases (See Non-Patent Document 2). There have been reports on similar suppression effects of oxidized coenzyme Q used in in vitro systems of nerve cells in which cell death is induced by exposure to hydrogen peroxide (See Non-Patent Documents 3 and 4).

However, no reports on efficacy of coenzyme Q in xerostomia have been made.

Patent Document 1: JP-A H07-330584
Patent Document 2: JP-A H07-330593
Patent Document 3: JP-A H07-287560

Non-Patent Document 1: J. Agric. Food Chem., 1999, Vol. 47, 3756-3763

Non-Patent Document 2: Free Radical Research, 2002, Vol. 36, 455-460

Non-Patent Document 3: Archives of Biochemistry and Biophysics, 2004, Vol. 421, 54-60

Non-Patent Document 4: Neurobiology of Disease, 2005, Vol. 18, 618-627

SUMMARY OF THE INVENTION

An object of the present invention is to provide an agent for relieving or preventing dryness or a dry feeling in the mouth of patients with xerostomia (dry mouth). Another object of the present invention is to provide a safe composition containing the relieving or preventing agent in a form of a food product, a health food, a dietary supplement, a supplement, a medicament, a quasi drug, a pet food, a feed or the like.

In order to solve the above-mentioned problems, the present inventors have intensively studied and found out that a composition containing an oxidized coenzyme Q and/or a reduced coenzyme Q as active ingredients exhibits an effect of increasing the amount of secreted saliva. The first aspect of the present invention relates to an agent for relieving or preventing xerostomia (dry mouth) containing an oxidized coenzyme Q and/or a reduced coenzyme Q as active ingredients.

The second aspect of the present invention relates to a food product, a health food, a dietary supplement, a supplement, an oral health care product, a medicament, a quasi drug, a pet food or a feed containing the relieving or preventing agent.

The third aspect of the present invention relates to a method for treating xerostomia, which comprises administering to a subject a composition containing an oxidized coenzyme Q and/or a reduced coenzyme Q as active ingredients.

The fourth aspect of the present invention relates to a method for reducing risks of xerostomia, which comprises administering to a subject a composition containing an oxidized coenzyme Q and/or a reduced coenzyme Q as active ingredients.

Hereinafter, the present invention will be described in detail.

In the present invention, the term "xerostomia" refers to a condition where the mouth becomes dry because of inhibited or diminished salivary secretion or aptyalia.

The term "xerostomia patient" used herein refers to one whose amount of secreted saliva is 2.0 g/2 min. or less as measured by Saxon test.

"Xerostomia pre-patients" include those who suffer from any diseases that cause organic change of salivary glands; those with pathological changes of salivary glands caused by a systemic disease, with a damaged salivary gland owing to radiotherapy, or with HIV infection (AIDS); those with secretory hypofunction owing to aging; those who take any drugs such as diuretics including trichloromethiazide and furosemide, hypotensors including reserpine and clonidine hydrochloride, anticholinergic agents including atropine sulfate, antihistamines including chlorophenylamine maleate, expectorant/cough suppressants, anti-Parkinson drugs, psychotropic drugs, antidepressants, tranquilizers and muscle relaxants; those who receive radiation therapy; and those who are under mental fatigue or stress, as well as those whose amount of secreted saliva is in a normal range but at a lower level, for example, 3.0 g/2 min. or less as measured by Saxon test.

Saxon test is performed as follows.

A test subject chews a piece of gauze for 2 minutes. The weight of the gauze piece has been measured in advance. After the 2-minute chewing, the weight of the gauze is measured. An amount of secreted saliva is calculated as a difference between the weights of the gauze piece before and after the 2-minute chewing.

The agent for relieving or preventing xerostomia of the first aspect of the present invention contains as active ingredients an oxidized coenzyme Q represented by the following formula (1) and/or a reduced coenzyme Q represented by the following formula (2).

Formula (1):

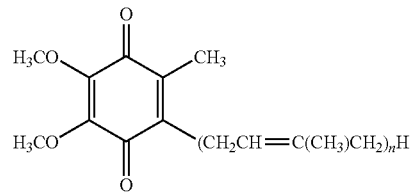

Formula (2):

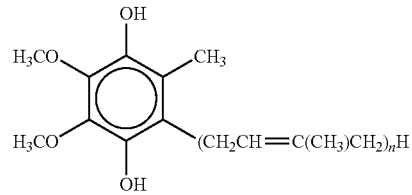

In the above formulas, n is an integer of 1 to 12.

The agent for relieving or preventing xerostomia of the present invention has effects to relieve symptoms associated with xerostomia mentioned above or to prevent occurrence of the symptoms. Examples of the symptoms associated with xerostomia include a dry feeling in the mouth, a burning feeling in the mouth, oral pain, glossodynia, dysgeusia, atrophy of lingual-papillae, oral mucosal inflammation, mouth sores, ulcers, cracked tongues, cracked mouth corner, difficulties in mastication, swallowing, phonation and speech, interrupted sleep and eating disorder. The agent for relieving or preventing xerostomia of the present invention also has effects to lower frequencies of occurrence of symptoms caused by xerostomia, such as dental disorders including oral mucous membrane ulcers, dental caries and periodontosis, oral infections and respiratory tract infections, to relieve symptoms such as bad breath, or to prevent onset of these symptoms.

The oxidized coenzyme Q used as an active ingredient of the agent for relieving or preventing xerostomia of the present invention may be prepared by methods conventionally known in the art such as fermentation methods, synthetic methods, and extraction methods from animals and plants. Considering safety, oxidized coenzymes Q with an all-trans structure prepared by any of these methods such as the fermentation methods except for the synthetic methods are desirable. Examples of those prepared by the fermentation methods include Kaneka Coenzyme $Q_{10}$ (registered trademark, product of Kaneka Corporation).

The method for preparing the reduced coenzyme Q used as an active ingredient of the agent for relieving or preventing xerostomia of the present invention is not particularly limited, and examples thereof include a method in which coenzyme Q is prepared by a conventional method, and then separated by liquid chromatography, and then the reduced coenzyme Q fraction obtained is condensed. Alternatively, a common reducing agent such as sodium borohydride or sodium dithionite (sodium hydrosulfite) may be optionally added to the above coenzyme Q to convert the oxidized coenzyme Q contained in the coenzyme Q into the reduced coenzyme Q by a usual reduction procedure, and then the reduced coenzyme Q being separated by liquid chromatography. Reduced coenzyme Q may also be prepared by a method in which the above-mentioned reducing agent is allowed to act on an available high purity coenzyme Q mainly composed of the oxidized coenzyme. Microorganism cells or the like microorganism-derived substances that contain reduced coenzyme Q may be used. Alternatively, oxidized coenzyme Q may be formulated with a substance having reducing ability such as vitamins to reduce the oxidized coenzyme Q so as to convert into the reduced coenzyme Q. KANEKA QH (registered trademark, product of KANEKA Corporation), a high purity reduced coenzyme $Q_{10}$, which was recently brought to market, can also be favorably used. Coenzyme Q that is a mixture of the oxidized coenzyme and the reduced coenzyme prepared by a method known in the art may be used without further treatment.

The agent for relieving or preventing xerostomia of the present invention may contain either of oxidized coenzyme Q and reduced coenzyme Q as an active ingredient. The agent may contain coenzyme Q, i.e. a mixture of oxidized coenzyme Q and reduced coenzyme Q, as an active ingredient. For the mixture, the ratio of the oxidized form and the reduced form in the coenzyme Q can be properly selected. When reduced coenzyme Q is used in an exceedingly high proportion of coenzyme Q, the coenzyme Q is expected to produce high relieving or preventive effects although it possibly leads to high cost for stabilization. The proportion of reduced coenzyme Q in the entire coenzyme Q is preferably 20% by weight or higher, more preferably 40% by weight or higher, and most preferably 80% by weight or higher. The term "coenzyme Q" used herein indicates any of an oxidized coenzyme Q alone, a reduced coenzyme Q alone, and a mixture of oxidized coenzyme Q and reduced coenzyme Q.

The ratio of the oxidized form and the reduced form in the coenzyme Q is normally determined by a method in which the oxidized coenzyme Q and the reduced coenzyme Q in a sample are quantified using an HPLC system provided with a UV detector and the ratio is calculated based on the quantities obtained; or a method of calculating the ratio of oxidized coenzyme Q and reduced coenzyme Q based on peak areas obtained by an HPLC system provided with an electrochemical detector. The system provided with an electrochemical detector enables specific measurement of oxidation-reduction substances at high sensitivity, and thereby is highly useful in measurement of the ratio of a reduced form that is present in a small amount in vivo or in a sample. All the ratios of oxidized coenzyme Q and reduced coenzyme Q illustrated in the present invention were quantified by the HPLC system provided with an electrochemical detector. Needless to say, the method for determining the ratio is not limited to that using this.

The coenzyme Q used in the agent for relieving or preventing xerostomia of the present invention is preferably coenzyme $Q_{10}$ with n=10 because coenzyme $Q_{10}$ is the predominantly occurring form of coenzyme Q in many mammals including humans.

The agent for relieving or preventing xerostomia of the present invention may contain coenzyme Q singly, or preferably contains a common edible fat and oil together with the coenzyme Q for lipophilicity of coenzyme Q. Specifically, the agent for relieving or preventing xerostomia of the present invention is preferably prepared by dispersing and dissolving coenzyme Q in a common edible fat and oil. Examples of the edible fat and oil include: coconut oil, palm oil, palm kernel oil, flaxseed oil, camellia oil, rice germ oil, avocado oil, rapeseed oil, rice oil, peanut oil, corn oil, wheat germ oil, soybean oil, perilla oil, cottonseed oil, sunflower seed oil, kapok oil, evening primrose oil, shea butter, sal fat, cacao butter, sesame oil, safflower oil, olive oil, lard, milk fat, fish oil, beef tallow, and processed fats and oils of these, medium-chain-fatty-acid triglyceride, and partial glycerides of fatty acids.

The agent for relieving or preventing xerostomia of the present invention may also be processed into a known form such as a cyclodextrin clathrate or an oil-in-water emulsion.

The agent for relieving or preventing xerostomia of the present invention may contain a nutritional supplement ingredient or a health food ingredient in addition to coenzyme Q.

The nutritional supplement ingredient is not particularly limited, and examples thereof include: amino acids, metal ions, saccharides, proteins, fatty acids, theanine, γ-aminobutyric acid (GABA), anserine, soybean peptides, thioredoxin, wheat gluten hydrolysates, glutamine, milk peptides, ω-3 fatty acids such as docosa-hexaenoic acid and eicosapentaenoic acid, phosphatidylserine, astaxanthin, polyphenols, green tea catechins, saponin, ginkgo biloba extracts, St. John's wort, *Apocynum venetum* extracts, Siberian ginseng, wasabi (Japanese horseradish), and lignans such as sesamin.

The health food ingredient is not particularly limited, and examples thereof include herbs, crude drugs, mushrooms, and extracts thereof. Examples of the herbs include, but are not limited to, Italian parsley, elecampane, olive, oregano, cardoon, chamomile, curry plant, catnip, caraway, Christmas rose, crimson clover, cornflower, common mallow, salad burnet, *santolina*, cinnamon, jasmine, *stevia*, sage, European linden, scented geranium, soapwort, Solomon's seal, thyme, tansy, chervil, chive, *nasturtium*, nutmeg, basil, honeysuckle, hyssop, flax, fennel, foxglove, black hollyhock, French marigold, betony, heliotrope, bergamot, hemp agrimony, rue, pot marigold, borage, white horehound, myrtle, mullein, marjoram, mint, yarrow, lavender, Lady's bedstraw, lemongrass, lemon verbena, lemon balm, rose, rosemary, rocket, wild strawberry, wild pansy, and forget-me-not. Examples of the crude drugs include, but are not limited to, *Rubiae Radix, Asini Corii Collas, Akebia quinata, Gambir, Epimedii Herba, Polygonati Odorati Rhizoma, Ginkgo biloba* L., *Clematidis Radix, Artemisiae Capillari Flos, Fennel, Termeric, Sepiae Endoconcha, Aconiti Radix, Mume Fructus, Linderae Radix, Limonitum, Corydalis Tuber, Astragali Radix, Scutellariae Radix, Polygonati Rhizoma, Phellodendri Cortex, Coptidis Rhizoma, Sinomeni Caulis* et *Rhizoma, Plantago asiatica* L., *Polygalae Radix, Sophorae Flos, Lygodii Spora, Achyranthis Radix, Erythrinae Cotex, Allii Macrostemi Bulbus, Artemisiae Folium, Prunellae Spica, Chebulae Fructus, Polygoni Multiflori Radix, Zedoariae Rhizoma, Pogostemi Herba, Puerariae Radix, Talcum, Torreyae Semen, Trichosanthis Radix, Trichosanthis Semen, Zingiberis Rhizoma, Glycyrrhizae Radix, Ecliptae Herba, Platycodi Radix, Chrysanthemi Flos, Aurantii Fructus, Aurantii Fructus Immaturus, Phellodendron amurense* Rupr., *Testudinis Plastrum, Cornu Bubali, Rhizoma* et *Radix Notopterygii, Armeniacae Semen, Polygonati Odorati Rhizoma, Rosae Laevigatae Fructus, Ginkgo Semen, Lonicerae Flos; Glechomae Herba, Desmodii Herba and Lysimachiae Herba; Agrimoniae Herba, Lycii Fructus, Sophorae Radix, Cibotii Rhizoma, Schizonepetae Spica Spatholobi Caulis and Millettia Reticulata, Cinnamomi Ramulus, Cinnamomi Cortex, Euryales Semen, Cassiae Semen, Pharbitidis Semen, Scrophulariae Radix, Sac-* charum Granorum, Carthami Flos, Albizziae Cortex, Lignum Dalbergia Odorifera, Semen Sojae Praeparata, Elsholtziae Herba and Moslae Herba, Cyperi Rhizoma, Magnoliae Cortex, Calculus Bovis, Acanthopanacis Cortex, Achyranthis Radix, Evodiae Fructus, Piperis Fructus, Drynariae Rhizoma, Semen Juglandis Regiae, Gallae Rhois, Succinum, Arctii Fructus, Sesami Semen, Schisandrae Fructus, Trigonellae Semen, Bupleuri Radix, Asiasari Radix, Saffron, Cynomorii Herba, Crataegi Fructus, Pseudbubus Cremastra Seu pleiones, Gardeniae Fructus, Bombycis Faeces, Corni Fructus, Zanthoxyli Fructus, Sophorae Subprostratae Radix, Semen Zizyphi Spinosae, Dioscoreae Rhizoma, Sparganii Rhizoma, Rehmanniae Radix, Asteris Radix, Violae Herba, Retinervus Luffae Fructus, Lycii Cortex, Arnebiae/Lithospermi Radix, Magnetitum, Fluoritum, Perilla, Perillae Fructus, Perillae Folium, Tribuli Fructus, Kochiae Fructus, Halloysitum Rubrum, Paeoniae Radix, Cnidii Monnieri Fructus, Adenophorae Radix, Plantaginis Semen, Plantaginis Herba, Eupolyphaga seu Opsithplatia, Leonuri Fructus, Amomi Semen, Zingiberis Rhizoma, Acori Graminei Rhizoma, Cimicifugae Rhizoma, Zanthoxyli Semen, Ligustri Fructus, Pheretima and Lumbricus, Magnoliae Flos, Massa Medicata Fermentata, Radix Gentianae Macrophyllae, Aquilariae Lignum, Hirudo, Rubiae Radix, Celosiae Semen, Indigo Naturalis, Citri Reticulatae Viride Pericarpium, Pyrrosiae Herba, Paeoniae Radix Rubra, Acori Graminei Rhizoma, Granati Pericarpium, Haliotidis Concha, Gypsum Fibrosum, Agrimoniae Herba, Chuanxiong Rhizoma, Peucedani Radix, Periostracum Cicadae, Inulae Flos, Toosendan Fructus, Amomi Tsao-ko Fructus, Gleditsiae Spina, Ramulus Mori Albae, Xanthii Fructus, Atractylodis Lanceae Rhizoma, Alpiniae Katsumadaii Semen, Mori Cortex, Mantidis Ootheca, Sappan Lignum, Perillae Herba, Rhei Rhizoma, Haematitum, Folium Daqingye, Zizyphi Fructus, Arecae Pericarpium, Alismatis Rhizoma, Lycopi Herba, Salviae Miltiorhizae Radix, Bambusae Caulis, Folium Phyllostachydis Henonis, Anemarrhenae Rhizoma, Uncariae Uncis Cum Ramulus, Polyporus Sclerotium, Aurantii Nobilis Pericarpium, Desurainiae Semen and Lepidii Semen, Radix Trichosanthis Kirilowii, Bambusae Concretio Silicea, Arisaematis Tuber, Gastrodiae Tuber, Asparagi Radix, Benincasae Semen, Angelicae Radix, Medulla Junci Effusi, Cordyceps, Angelicae Radix, Persicae Semen, Cuscutae Semen, Eucommiae Cortex, Cistanches Herba, Myristicae Semen, Olibanum, Ginseng Radix, Lonicerae Folium Cum Caulis, Ligustri Fructus, Brassicae Semen, Hordei Fructus Germinatus, Platycladi Semen, Amomi Rotundus Fructus, Dictamni Radicis Cortex, Pulsatillae Radix, Lablab Semen album, Ophiopogonis Tuber, Morindae Radix, Menthae Herba, Glehniae Radix Cum Rhizoma, Pinelliae Tuber, Croci Stigma, Rhizoma Dioscoreae hypoglaucae, Torreyae Semen, Lilii Bulbus, Radix Angelicae Dahuricae, Atractylodis Rhizoma, Radix Angelicae Dahuricae, Atractylodis Rhizoma, Santali Lignum, Cynanchi Atrati Radix, Stemonae Radix, Herba Hedyotis Diffusae, Bletillae Rhizoma, Bombyx Batryticatus, Arecae Semen, Rubi Fructus, Poria, Aconiti Tuber, Amydae Testudo, Carthami Flos, Herba Polygoni Avicularis, Radix Stephaniae Tetrandrae and Sinomeni Caulis et Rhizoma, Imperatae Rhizoma, Saposhnikoviae Radix, Typhae Pollen, Taraxaci Herba, Psoraleae Semen, Moutan Cortex, Ostreae Concha, Rosae Rugosae Flos, Ephedrae Herba, Ephedrae Radix, Cannabis Fructus, Viticis Fructus, Buddleiae Flos, Chebulae Fructus, Akebiae Caulis, Equiseti Herba, Chaenomelis Fructus, Saussureae Radix, Belamcandae Rhizoma, Alpiniae Fructus, Leonuri Herba, Caulis Polygoni Multiflori, Fel Ursi, Coicis Semen, Artemisiae Argyi Folium, Omphalia, Raphani Semen, Momordicae Fructus, Longan Arillus, Herba Artemisiae Anomalae, Fossilia Ossis Mastodi, Gentianae Scabrae Radix, Alpiniae Officinari Rhizoma, Semen Phaseoli, Forsythiae Fructus, Glechomae Herba, Nelumbis Semen, Cervi Parvum Cornu, and Nidus Vespae. Examples of the mushrooms include Tricholoma matsutake, Grifola frondosa, Lentinus edodes, Flammulina veluptipes, Lyophyllum sp., Pleurotus eryngii, and Mycoleptodonoides aitchisonii.

The agent for relieving or preventing xerostomia of the present invention may further contain an antioxidant or an antioxidant enzyme in addition to the coenzyme Q. The antioxidant is not particularly limited, and examples thereof include: Vitamin E, Vitamin E derivatives, Vitamin C, Vitamin C derivatives, lycopene, Vitamin A, carotenoids, Vitamin B, Vitamin B derivatives, flavonoids, glutathione, α-lipoic acid, and selenium. The antioxidant enzyme is not particularly limited, and examples thereof include: superoxide dismutase (SOD), glutathione peroxidase, glutathione-S-transferase, glutathione reductase, catalase, and ascorbic acid peroxidase.

Only one of, or a suitable combination of two or more of the antioxidants, the antioxidant enzymes, the nutritional supplement ingredients, and the health food ingredients described above can be used in the agent for relieving or preventing xerostomia of the present invention.

The amount of the antioxidants, the antioxidant enzymes, the nutritional supplement ingredients and/or the health food ingredients in the agent for relieving or preventing xerostomia of the present invention is not particularly limited, and preferably 1 to 10,000% by weight, and more preferably 10 to 1,000% by weight per 100% by weight of the total coenzyme Q amount (total amount of oxidized coenzyme Q and reduced coenzyme Q). When the amount is less than 1% by weight per 100% by weight of the total coenzyme Q amount, combined use of these ingredients produces a small effect. When it exceeds 10,000% by weight, the relative amount of coenzyme Q is low, thereby possibly resulting in failure to produce the effects of the present invention sufficiently.

The total amount of coenzyme Q contained in the relieving or preventing agent of the present invention is not particularly limited, and is normally 1 to 100% by weight per 100% by weight of the total weight of the relieving or preventing agent, preferably 5 to 80% by weight, and more preferably 10 to 60% by weight.

In addition to the above-mentioned ingredients, the relieving or preventing agent for xerostomia of the present invention may be optionally added with other ingredients such as pharmaceutically acceptable ingredients or ingredients acceptable as foods by an ordinary method. These ingredients are not particularly limited, and examples thereof include vehicles, disintegrating agents, lubricants, binders, anti-oxidizing agents, colorants, anti-aggregating agents, absorption promoters, solubilizing agents, stabilizers, and revitalizing ingredients.

The vehicles are not particularly limited, and examples thereof include white sugar, lactose, glucose, cornstarch, mannitol, crystalline cellulose, calcium phosphate, and calcium sulfate. The disintegrating agents are not particularly limited, and examples thereof include starch, agar, calcium citrate, calcium carbonate, sodium bicarbonate, dextrin, crystalline cellulose, carboxymethyl cellulose, and tragacanths. The lubricants are not particularly limited, and examples thereof include talc, magnesium stearate, polyethylene glycols, silica, and hydrogenated vegetable oils. The binders are not particularly limited, and examples thereof include ethyl cellulose, methyl cellulose, hydroxypropyl methylcellulose, tragacanths, shellac, gelatin, gum arabic, polyvinyl pyrrolidone, polyvinyl alcohol, polyacrylic acid, polymethacrylic acid, and sorbitol. The anti-oxidizing agents are not particularly limited, and examples thereof include ascorbic acid, tocopherol, vitamin A, β-carotene, sodium hydrogen sulfite, sodium thiosulfate, sodium pyrosulfite, and citric acid. The colorants are not particularly limited, and examples thereof include pharmaceutically acceptable colorants. The anti-aggregating agents are not particularly limited, and examples thereof include stearic acid, talc, light anhydrous silicic acid, and hydrous silicon dioxide. The absorption promoters are not particularly limited, and examples thereof include surfactants such as higher alcohols, higher fatty acids, and glycerin fatty acid esters. The solubilizing agents are not particularly limited, and examples thereof include organic acids such as fumaric acid, succinic acid, and malic acid. The stabilizers are not particularly limited, and examples thereof include benzoic acid, sodium benzoate, and ethyl parahydroxybenzoate. The revitalizing ingredients are not particularly limited, and examples thereof include creatine, taurine, vitamin $B_1$, vitamin B derivatives, amino acids and mixtures thereof.

The agent for relieving or preventing xerostomia of the present invention may be administered as is, or may be processed into a composition containing the relieving or preventing agent in a form of a food product, a health food, a dietary supplement, a supplement, an oral health care product, a medicament, a quasi drug, a pet food or a feed. The term "health food" used herein refers to food products in all forms that can be taken in for health maintenance except for medicaments, and includes so-called health foods, health supplements, foods for specified health use, foods with nutrient function claims and the like. These compositions are the second aspect of the present invention.

The formulation of the relieving or preventing agent of the present invention is not particularly limited, and examples thereof include: orally administrable forms such as capsules, microcapsules, soft capsules, tablets, powders, chewables, syrups, and liquid preparations; common food product forms such as edible-fat-and-oil compositions, cooking oils, spray oils, butters, margarines, shortenings, whipped creams, concentrated milks, whiteners, dressings, pickling liquids, breads, cakes, pies, cookies, Japanese sweets, snacks, fried snacks, chocolates, chocolate confectioneries, rice confectioneries, roux, sauces, bastes, toppings, iced desserts, noodles, bakery mixes, fried food products, processed meat products, fish cakes, frozen foods including frozen entrees, frozen livestock food products, and frozen agricultural foods, cooked rice, jams, cheeses, cheese foods, cheese-like products, gums, candies, fermented milks, canned foods, and beverages; and forms that allow an effective ingredient to be delivered into the body through the skin, such as adhesive skin patches, lotions, and sprays. Particularly in a form of the oral health care products, examples of the formulation include toothpastes, mouthwashes, and oral sprays.

The third aspect of the present invention relates to a method for treating xerostomia, which comprises administering to a subject a composition containing an oxidized coenzyme Q and/or a reduced coenzyme Q as active ingredients.

The way of administration of the composition is not particularly limited, and example thereof include oral administration, intravenous administration, intramuscular administration, intraspinal administration, subcutaneous administration, sublingual administration, transrectal administration, transvaginal administration, eye drop administration, transnasal administration, inhalation, transdermal administration, and transdermal absorption administration. Among them, oral administration is preferable because it is the most convenient and safest.

The subject to be administered is preferably a xerostomia patient or a xerostomia pre-patient.

The formulation of the composition to be administered is not particularly limited, and examples thereof include: orally administrable forms such as capsules, microcapsules, soft capsules, tablets, powders, chewables, syrups and liquid preparations; common food product forms such as edible-fat-and-oil compositions, cooking oils, spray oils, butters, margarines, shortenings, whipped creams, concentrated milks, whiteners, dressings, pickling liquids, breads, cakes, pies, cookies, Japanese sweets, snacks, fried snacks, chocolates, chocolate confectioneries, rice confectioneries, roux, sauces, bastes, toppings, iced desserts, noodles, bakery mixes, fried food products, processed meat products, fish cakes, frozen foods including frozen entrees, frozen livestock food products, and frozen agricultural foods, cooked rice, jams, cheeses, cheese foods, cheese-like products, gums, candies, fermented milks, canned foods, and beverages; and forms that allow an effective ingredient to be delivered into the body through the skin, such as adhesive skin patches, lotions, and sprays. Particularly when administered in a form of oral health care products, examples of the formulation include toothpastes, mouthwashes, and oral sprays.

When the composition of the present invention contains only an oxidized coenzyme Q of coenzyme Q as an active ingredient (namely, free of a reduced form), the effective dose of the oxidized coenzyme Q per day for adults is 50 to 1000 mg, preferably 100 to 600 mg, and more preferably 200 to 350 mg. A dose of less than 50 mg may fail to sufficiently produce relieving or preventive effects for xerostomia. However, the effective dose is known to vary depending on the formulation of preparation. A highly absorbable preparation is expected to bring desired results even when administered at a lower dose. When the composition contains only a reduced coenzyme Q of coenzyme Q as an active ingredient (namely, free of an oxidized form), the effective dose of the reduced coenzyme Q per day for adults is 10 to 500 mg, preferably 30 to 300 mg, and more preferably 50 to 150 mg. When the composition contains a mixture of an oxidized coenzyme Q and a reduced coenzyme Q as an active ingredient, the total effective dose per day of the oxidized coenzyme Q and reduced coenzyme Q cannot be simply determined because it varies depending on the ratio of oxidized coenzyme Q and reduced coenzyme Q. However, the total effective dose for adults is 10 to 450 mg, preferably 20 to 300 mg, and more preferably 30 to 200 mg. Reduced coenzyme Q is known to be superior in oral and mucosal absorbabilities in comparison to the oxidized coenzyme Q. Therefore, even at a lower dose than the oxidized coenzyme Q, the reduced coenzyme Q can produce the equivalent effects.

The fourth aspect of the present invention relates to a method for reducing risks (risks of onset or recurrence) of xerostomia, which comprises administering to a subject a composition containing an oxidized coenzyme Q and/or a reduced coenzyme Q as active ingredients.

The way of administration of the composition is not particularly limited, and examples thereof include the same administrations as those listed for the method for treating xerostomia. The subject, the formulation and the dose are similarly determined.

The agent for relieving or preventing xerostomia of the present invention increases salivary secretion, and thereby produces significant effects in relieving and preventing the symptoms of xerostomia induced by various causes. The agent for relieving or preventing xerostomia of the present invention produces no side effects and can be taken on a daily basis. The composition containing the agent for relieving or preventing xerostomia of the present invention is useful as a food product, a health food, a dietary supplement, a supplement, an oral health care product, a medicament, a quasi drug, a pet food or a feed. In the method for treating xerostomia, and the method for reducing risks of xerostomia, administration to a subject of a composition containing an oxidized coenzyme Q and/or a reduced coenzyme Q as active ingredients enables effectively increasing salivary secretion.

BEST MODE FOR CARRYING OUT THE INVENTION

Hereinafter, the present invention will be described in more detail by way of examples. However, the present invention is not limited only to these examples.

EXAMPLE 1

Salivary Secretion-Increasing Effect by Coenzyme $Q_{10}$ Intake in Patients with Xerostomia In total 23 xerostomia (dry mouth) outpatients (23 females including 21 Sjogren syndrome patients) were divided into three groups. To one group consisting of 9 patients, one oxidized coenzyme $Q_{10}$-containing capsule having the composition illustrated in Table 1 (Test food 1, 240 mg per capsule) was administered every day for one month. To another group consisting of another 9 patients, one reduced coenzyme $Q_{10}$-containing capsule having the composition shown in Table 1 (Test food 2, 240 mg per capsule) was administered every day for one month. The amount of secreted saliva was measured for each group before and after the intake. To the other group consisting of remaining 5 patients, one placebo capsule (Control food, 240 mg per capsule) was administered every day for one month. The amount of secreted saliva was similarly measured before and after the intake.

The amount of secreted saliva was measured by Saxon test. Namely, a test subject chewed a piece of gauze for 2 minutes. The weight of the gauze piece had been measured in advance. After the 2-minute chewing, the weight of the gauze piece was measured. The amount of secreted saliva was calculated as a difference between the weights of the gauze piece before and after the 2-minute chewing. In the present example, those whose amount of secreted saliva measured by Saxon test was 2.0 g/2 min. or less were determined as xerostomia patients, and those whose amount of secreted saliva was more than that were determined as healthy persons. Tables 2 and 3 illustrate the average values of all subjects of each group.

TABLE 1

Formulations of Compositions
Test food composition (per 4-oval soft capsule)

| Ingredients | Test food 1 | Test food 2 | Control food |
|---|---|---|---|
| Oxidized coenzyme $Q_{10}$ (mg) | 100 | — | — |
| Reduced coenzyme $Q_{10}$ (mg) | — | 100 | — |
| Safflower oil (mg) | 134.67 | 134.67 | 234.67 |
| Beeswax (mg) | 4.33 | 4.33 | 4.33 |
| Poem S-100 (mg) | 0.6 | 0.6 | 0.6 |
| Soybean lecithin (mg) | 0.4 | 0.4 | 0.4 |

* Poem S-100 (emulsifier containing glyceryl monostearate, product of Riken Vitamin Co., Ltd.)

TABLE 2

Amount of secreted saliva (g/2 min.)

| Samples | Before intake | After intake | Increased amount |
|---|---|---|---|
| Placebo | 0.73 | 0.95 | 0.22 |
| Oxidized coenzyme $Q_{10}$ | 0.69 | 1.28* | 0.59 |
| Reduced coenzyme $Q_{10}$ | 0.82 | 1.52* | 0.70 |

*$p < 0.05$ Student t-test

Table 2 illustrates the results. The amounts of saliva secreted before and after the oxidized coenzyme $Q_{10}$ intake obtained in this test were 0.69 g/2 min and 1.28 g/2 min., respectively. Salivary secretion significantly increased with a difference of 0.59 g/2 min. The amounts of saliva secreted before and after the reduced coenzyme $Q_{10}$ intake were 0.82 g/2 min. and 1.52 g/2 min., respectively. Salivary secretion increased with a significant difference of 0.7 g/2 min. Thus, it was found that reduced coenzyme $Q_{10}$ produced higher effects than oxidized coenzyme $Q_{10}$.

REFERENCE EXAMPLE 1

Salivary Secretion-Increasing Effect by Coenzyme $Q_{10}$ Intake in Healthy Person In total, 57 healthy persons (12 males, 45 females) were collected as volunteers. One oxidized coenzyme $Q_{10}$-containing capsule having the composition illustrated in Table 1 (Test food 1, 240 mg per capsule) was administered every day for one month to a group consisting of 22 healthy persons (5 males, 17 females), and one reduced coenzyme $Q_{10}$-containing capsule having the composition illustrated in Table 1 (Test food 2, 240 mg per capsule) was administered every day for one month to another group consisting of 22 healthy persons (5 males, 17 females). The amount of secreted saliva was measured for each group before and after the intake by the same procedure as that in Example 1. To remaining 13 healthy persons (2 males, 11 females), one placebo capsule (Control food, 240 mg per capsule) was administered every day for one month. The amount of secreted saliva was measured before and after the intake.

TABLE 3

Amount of secreted saliva (g/2 min.)

| Samples | Before intake | After intake | Increased amount |
|---|---|---|---|
| Placebo | 5.48 | 6.05 | 0.57 |
| Oxidized coenzyme $Q_{10}$ | 5.73 | 6.16 | 0.43 |
| Reduced coenzyme $Q_{10}$ | 3.44 | 3.54 | 0.10 |

Table 3 illustrates the results. None of the oxidized coenzyme $Q_{10}$ capsule administration group, the reduced coenzyme $Q_{10}$ capsule administration group and the placebo capsule administration group showed a significant or excessive increase between the amounts of secreted saliva before and after the intake in this test.

EXAMPLE 2

Increasing Effects of Salivary Secretion and Coenzyme $Q_{10}$ Concentration in Saliva by Oxidized Coenzyme $Q_{10}$-containing Gum Intake in Patient with Xerostomia In total, 12 xerostomia (dry mouth) outpatients were studied by a test in which they chewed an oxidized coenzyme $Q_{10}$-containing gum (120 mg of oxidized coenzyme $Q_{10}$ in 10 pieces) immediately after eating and drinking for at least 5 minutes (10 pieces per day, 2 pieces per time, i.e. 5 times per day). The test was continued for 2 weeks. The amount of secreted saliva was measured before and after the 2-week continuous intake by the same procedure as that in Example 1. The amount of saliva secreted before the oxidized coenzyme $Q_{10}$-containing gum intake was 0.78 g/2 min., and the amount of saliva secreted after the 2-week continuous gum intake was 1.18 g/2 min. Salivary secretion increased by 0.40 g/2 min. This improvement effect was statistically significant, that is, the difference was found to be significant by Student t-test.

FORMULATION EXAMPLE 1

Powder

Oxidized coenzyme $Q_{10}$ was dissolved in propanol and allowed to adsorb on microcrystalline cellulose. Subsequently, the obtained mixture was dried under a reduced pressure, and then mixed with cornstarch to give a powder.

| | |
|---|---|
| Oxidized coenzyme $Q_{10}$ | 20 parts by weight |
| Microcrystalline cellulose | 40 parts by weight |
| Cornstarch | 55 parts by weight |

FORMULATION EXAMPLE 2

Capsule

A powder having the following formulation was prepared by the same procedure as that in Formulation Example 1, and then filled into gelatin capsules by an ordinary method.

| | |
|---|---|
| Oxidized coenzyme $Q_{10}$ | 20 parts by weight |
| Microcrystalline cellulose | 40 parts by weight |
| Cornstarch | 20 parts by weight |
| Lactose | 65 parts by weight |
| Magnesium stearate | 3 parts by weight |
| Polyvinyl pyrrolidone | 2 parts by weight |

FORMULATION EXAMPLE 3

Soft Capsule

Corn oil was warmed to 50° C., and thereto was added oxidized coenzyme $Q_{10}$ melted at the same temperature and dissolved. The obtained solution was encapsulated into soft capsules by an ordinary method.

| | |
|---|---|
| Oxidized coenzyme $Q_{10}$ | 50 parts by weight |
| Corn oil | 350 parts by weight |

FORMULATION EXAMPLE 4

Tablet

Oxidized coenzyme $Q_{10}$ was dissolved in propanol and allowed to adsorb on microcrystalline cellulose. Subsequently, the obtained mixture was dried under a reduced pressure. This mixture was mixed with cornstarch, lactose, carboxymethylcellulose calcium and magnesium stearate under a nitrogen atmosphere, and then added with a polyvinyl pyrrolidone aqueous solution as a binder. The resultant mixture was formed into granules by an ordinary method. These granules were added with talc as a lubricant and mixed, and thereafter formed into tablets.

| | |
|---|---|
| Oxidized coenzyme $Q_{10}$ | 20 parts by weight |
| Cornstarch | 20 parts by weight |
| Lactose | 15 parts by weight |
| Carboxymethylcellulose calcium | 10 parts by weight |
| Microcrystalline cellulose | 40 parts by weight |
| Polyvinyl pyrrolidone | 5 parts by weight |
| Magnesium stearate | 3 parts by weight |
| Talc | 10 parts by weight |

FORMULATION EXAMPLE 5

Capsule

A powder having the following formulation was prepared by the same procedure as that in Formulation Example 1, and then filled into gelatin capsules by an ordinary method. The filled capsules were sealed, and packed under a nitrogen atmosphere, and thereafter refrigerated.

| | |
|---|---|
| Reduced coenzyme $Q_{10}$ | 20 parts by weight |
| Oxidized coenzyme $Q_{10}$ | 0.4 parts by weight |
| Microcrystalline cellulose | 40 parts by weight |
| Cornstarch | 20 parts by weight |
| Lactose | 65 parts by weight |
| Magnesium stearate | 3 parts by weight |
| Polyvinyl pyrrolidone | 2 parts by weight |

FORMULATION EXAMPLE 6

Soft Capsule

Corn oil was warmed to 50° C., and thereto was added reduced coenzyme $Q_{10}$ (containing 2% of oxidized coenzyme $Q_{10}$) melted at the same temperature and dissolved. The obtained solution was encapsulated into soft capsules by an ordinary method.

| | |
|---|---|
| Reduced coenzyme $Q_{10}$ | 49 parts by weight |
| Oxidized coenzyme $Q_{10}$ | 1 part by weight |
| Corn oil | 350 parts by weight |

FORMULATION EXAMPLE 7

Capsule

A powder having the following formulation was prepared by the same procedure as that in Formulation Example 1, and then filled into gelatin capsules by an ordinary method. The filled capsules were sealed, and packed under a nitrogen atmosphere, and thereafter refrigerated.

| | |
|---|---|
| Oxidized coenzyme $Q_{10}$ | 20 parts by weight |
| Vitamin B | 20 parts by weight |
| Vitamin C | 40 parts by weight |
| Vitamin E | 20 parts by weight |
| Microcrystalline cellulose | 40 parts by weight |
| Cornstarch | 20 parts by weight |
| Lactose | 65 parts by weight |
| Magnesium stearate | 3 parts by weight |
| Polyvinyl pyrrolidone | 2 parts by weight |

FORMULATION EXAMPLE

Capsule

A powder having the following formulation was prepared by the same procedure as that in Formulation Example 1, and then filled into gelatin capsules by an ordinary method. The filled capsules were sealed, and packed under a nitrogen atmosphere, and thereafter refrigerated.

| | |
|---|---|
| Reduced coenzyme $Q_{10}$ | 20 parts by weight |
| Oxidized coenzyme $Q_{10}$ | 1 part by weight |
| Vitamin B | 20 parts by weight |
| Vitamin C | 40 parts by weight |
| Vitamin E | 20 parts by weight |
| Microcrystalline cellulose | 40 parts by weight |
| Cornstarch | 20 parts by weight |
| Lactose | 65 parts by weight |
| Magnesium stearate | 3 parts by weight |
| Polyvinyl pyrrolidone | 2 parts by weight |

Industrial Applicability

The composition containing an oxidized coenzyme Q and/or a reduced coenzyme Q of the present invention increases salivary secretion, and thereby enables relief or prevention of xerostomia.

The present invention can provide medicaments, quasi drugs, food products, nutritional supplements, compositions for oral health care, compositions for animal medicines, pet foods and feeds containing the composition.

The invention claimed is:

1. A method for treating xerostomia,
which comprises administering to a subject a composition containing as active ingredients an oxidized coenzyme Q represented by the following formula (1):

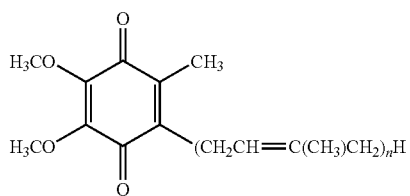

wherein n is an integer of 1 to 12, and/or a reduced coenzyme Q represented by the following formula (2):

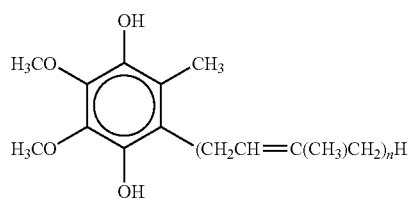

wherein n is an integer of 1 to 12.

2. The method according to claim 1,
wherein the subject is a xerostomia patient or a xerostomia pre-patient.

3. A method for reducing risks of xerostomia,
which comprises administering to a subject a composition containing as active ingredients an oxidized coenzyme Q represented by the following formula (1):

$$\text{(1)}$$

$$\begin{array}{c}\text{H}_3\text{CO} \\ \text{H}_3\text{CO}\end{array} \diagup\!\!\!\diagdown \begin{array}{c}\text{CH}_3 \\ (\text{CH}_2\text{CH}\!=\!\text{C}(\text{CH}_3)\text{CH}_2)_n\text{H}\end{array}$$

wherein n is an integer of 1 to 12, and/or a reduced coenzyme Q represented by the following formula (2):

$$\text{(2)}$$

$$\begin{array}{c}\text{H}_3\text{CO} \\ \text{H}_3\text{CO}\end{array} \diagup\!\!\!\diagdown \begin{array}{c}\text{OH} \\ \text{CH}_3 \\ (\text{CH}_2\text{CH}\!=\!\text{C}(\text{CH}_3)\text{CH}_2)_n\text{H} \\ \text{OH}\end{array}$$

wherein n is an integer of 1 to 12.

4. The method according to claim 3,
wherein the subject is a xerostomia patient or a xerostomia pre-patient.

* * * * *